(12) United States Patent
Boese et al.

(10) Patent No.: US 8,099,155 B2
(45) Date of Patent: Jan. 17, 2012

(54) METHOD FOR ASSISTING WITH PERCUTANEOUS INTERVENTIONS

(75) Inventors: Jan Boese, Eckental (DE); Estelle Camus, Mountain View, CA (US); Matthias John, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 422 days.

(21) Appl. No.: 12/229,332

(22) Filed: Aug. 21, 2008

(65) Prior Publication Data
US 2009/0326373 A1 Dec. 31, 2009

(30) Foreign Application Priority Data
Jun. 25, 2008 (DE) .......................... 10 2008 030 244

(51) Int. Cl.
*A61B 5/00* (2006.01)
(52) U.S. Cl. ............ 600/427; 600/443; 600/461; 378/4; 382/131
(58) Field of Classification Search .................. 600/407, 600/424, 425, 427, 429, 437, 440, 443, 461, 600/464; 606/130; 378/4; 382/131
See application file for complete search history.

(56) References Cited

U.S. PATENT DOCUMENTS

| | | | |
|---|---|---|---|
| 2001/0025183 A1* | 9/2001 | Shahidi | 606/130 |
| 2006/0074287 A1* | 4/2006 | Neumann et al. | 600/407 |
| 2006/0195033 A1* | 8/2006 | Akimoto et al. | 600/429 |
| 2007/0027390 A1 | 2/2007 | Maschke et al. | |

FOREIGN PATENT DOCUMENTS
DE 102005032755 A1 1/2007

OTHER PUBLICATIONS

Meyer et al., "Schichtbasierte Illustration medizinischer Volumendaten zur intraoperativen Navigation", Bildverarbeitung für die Medizin, pp. 335-339. Springer-Verlag, 2006. wwwisg.cs.uni-magdeburg.de/cv/pub/files/BVM2006_BjoernMeyer.pdf; Others; 2006.

Barry et al.; "Three-dimensional freehand ultrasound : Image reconstruction and volume analysis", Ultrasound in medicine & biology, vol. 23, No. 8, pp. 1209-1224,Received Feb. 17, 1997; accepted Jun. 17, 1997; Others; 1997.

Hajnal et al., "Medical Image Registration", The Biomedical Engineering Series, 2007, pp. 1-70, CRC Press.

* cited by examiner

*Primary Examiner* — Brian Casler
*Assistant Examiner* — Amanda Lauritzen

(57) ABSTRACT

The present invention relates to a method for assisting with percutaneous interventions, wherein 2D x-ray images of an object region are recorded before the intervention using a C-arm x-ray system or a robot-based x-ray system at different projection angles and 3D x-ray image data of the object region is reconstructed from the 2D x-ray recordings. One or more 2D or 3D ultrasound images are recorded before and/or during the intervention using an external ultrasound system and registered with the 3D image data. The 2D or 3D ultrasound images are then overlaid with the 3D image data record or a target region segmented therefrom or displayed next to one another in the same perspective. The method allows a puncture or biopsy to be monitored with a low level of radiation.

20 Claims, 1 Drawing Sheet

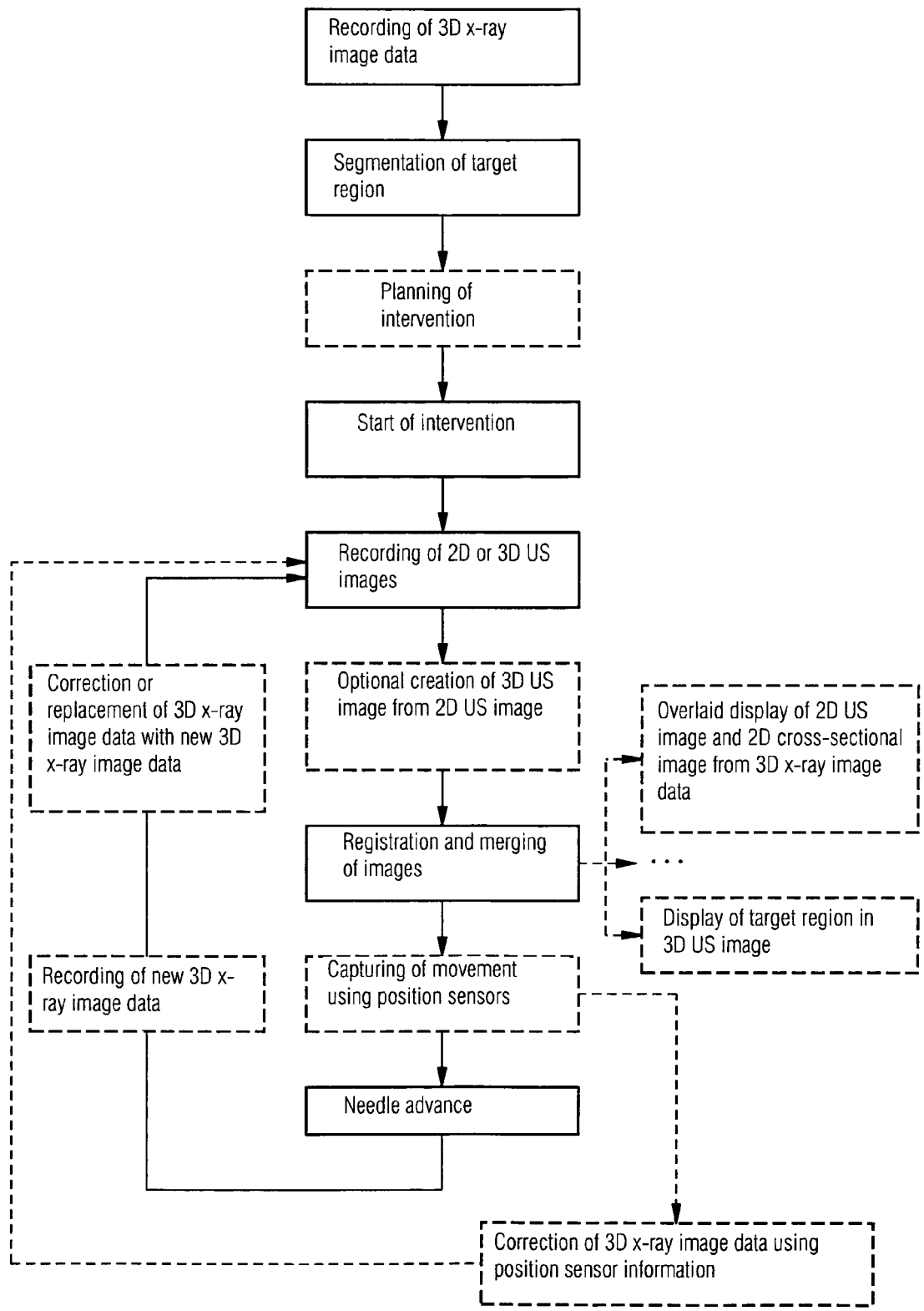

METHOD FOR ASSISTING WITH PERCUTANEOUS INTERVENTIONS

CROSS REFERENCE TO RELATED APPLICATIONS

This application claims priority of German application No. 10 2008 030 244.9 filed Jun. 25, 2008, which is incorporated by reference herein in its entirety.

FIELD OF THE INVENTION

The present invention relates to a method for assisting with percutaneous interventions, wherein a 3D image data record of an object region including the target region is produced before the intervention and the intervention is monitored using real-time imaging.

BACKGROUND OF THE INVENTION

Percutaneous method, e.g. biopsies or punctures play an important role in the diagnosis and treatment of various diseases. The principle of a percutaneous intervention is based on the puncturing of a pathological process, for example a tumor in the liver, through the skin. In this process tissue samples can be taken for diagnostic purposes for example using special biopsy needles. Percutaneous interventions also allow a therapy, for example the TIPSS procedure (TIPSS: transcutaneous intrahepatic porto-systemic shunt), the drainage of an abscess or the thermoablation of a solitary liver metastasis, to be carried out. A percutaneous puncture generally takes place after prior imaging diagnosis using computed tomography (CT), magnetic resonance tomography (MRT) or ultrasound and is monitored and controlled during the interventions by means of real-time imaging.

Because they are minimally invasive, use reliable access paths and allow local therapy, percutaneous interventions will be carried out with increasing frequency in coming years. Improved diagnosis allows potential pathologies to be discovered at increasingly early stages and increasingly small disease centers to be punctured in positions that are difficult to access. Nevertheless percutaneous diagnosis and therapy still have some limitations. The literature indicates a complication rate between 3.9% and 23.9%. These are predominantly non-life-threatening bleeding, hematomas, pneumothoraces or organ damage. However there is still a risk of dying from such an intervention, in particular if a major vessel has been damaged accidentally. Puncture error is a further serious problem. The rate of incorrect or incomplete punctures is given as up to 30% in the literature. Puncture errors can result in false negative diagnoses or an inadequate therapeutic dosage in the required target region. The number of incorrect punctures must therefore be kept as low as possible both in the interests of the patient and from the point of view of effective and economical medicine.

The problem with a precise puncture lies in the variability of the target region due to respiratory movement, displacement and deformation of organs and the disease center due to the advance of the needle and possible unpredictable patient movement.

DE 10 2005 032 755 A1 therefore describes a system for carrying out and monitoring minimally invasive interventions, wherein 2D x-ray images of an object region are recorded at different projection angles using a C-arm x-ray system and 3D image data of the object region is reconstructed from the 2D x-ray recordings. The same x-ray system can then be used during the intervention to record 2D images in real time and to overlay them on the display of the 3D image data. This system can also be used to carry out 3D ultrasound recordings in real time using an ultrasound catheter and to register and display said recordings with the high-resolution 3D image data of the C-arm x-ray device.

However with the last-mentioned method either the deposition of ionizing radiation during the intervention must be taken into account for the patient or the application is limited to certain regions in the case of the ultrasound catheter. In particular biopsies and punctures can generally not be carried out using an ultrasound catheter.

SUMMARY OF THE INVENTION

The object of the present invention is to specify a method for assisting with percutaneous interventions, which is suitable for monitoring biopsies and punctures and which reduces the radiation load for the patient during the intervention.

The object is achieved with the method as claimed in the independent claim. Advantageous embodiments of the method are set out in the dependent claims or will emerge from the description which follows and the exemplary embodiment.

With the proposed method for assisting with percutaneous interventions 2D x-ray images of an object region are recorded before the intervention with a first resolution using a C-arm x-ray system or a robot-based x-ray system at different projection angles and 3D x-ray image data of the object region is reconstructed from the 2D x-ray recordings. The C-arm x-ray system can be the Siemens DynaCT® system for example. The target region for the intervention is segmented in the reconstructed 3D image data. One or more 2D or 3D ultrasound images containing at least a part of the said object region are then recorded before and/or during the intervention using an external ultrasound system, and registered with the 3D x-ray image data. The 2D or 3D ultrasound images are recorded with a lower resolution than the 3D x-ray image data using the x-ray system. The 2D or 3D ultrasound images are then overlaid during the intervention with the 3D x-ray image data and/or the target region segmented therefrom or displayed separately therefrom in the same perspective.

With the proposed method ultrasound imaging with an external ultrasound device is thus combined with 3D x-ray imaging using a C-arm x-ray system or a robot-based x-ray system. An external ultrasound system here refers to an ultrasound system, which is arranged outside the body and is therefore not inserted into the body. A robot-based x-ray system has an imaging system guided by one or more robot arms. With the robot-based x-ray system 2D x-ray images of the object region can be recorded at different projection angles in the same manner as with an x-ray C-arm system, these then being used to reconstruct a 3D x-ray image data record. Ultrasound imaging during the intervention has the advantage of imaging in real time without a radiation load for the patient. On the other hand high resolution is achieved with the x-ray imaging carried out before the intervention. The combination of the C-arm or robot-based x-ray system with external ultrasound imaging has the advantage that in many instances registration can be simpler than when using a CT system, which generally requires the patient to be moved from room to room for the CT recording and the intervention. The C-arm x-ray system or robot-based x-ray system in contrast provides very easy access to the patient and can therefore be deployed in the same room, in which the intervention also takes place. Spatial registration of the ultrasound system and x-ray system is therefore simplified significantly.

There are different variants of ultrasound imaging, with the examples that follow not representing a conclusive list. In one embodiment therefore an ultrasound head can be deployed, generating two-dimensional images. By moving the ultrasound head in a controlled manner to record different 2D images, it is possible to obtain a data record, from which it is possible to generate a 3D image by placing the 2D images thus recorded behind one another taking into account their known recording position. The third dimension is hereby obtained through knowledge of the movement data of the ultrasound head when the individual images are recorded.

In a further embodiment an ultrasound head can be deployed, which generates two-dimensional images and can be moved by machine. Movement by machine allows a three-dimensional volume to be scanned evenly. The three-dimensional image data record is created in the same manner here as with the previous embodiment.

According to a further embodiment an ultrasound head can be deployed, which generates two-dimensional images and is equipped with a position sensor. This ultrasound head can be moved both manually and by machine, it being possible for the images to be spatially assigned in real time to create a 3D image by way of the captured positions.

In a further embodiment an ultrasound head with a rotatable 2D array is deployed, which can generate three-dimensional images directly by controlled rotation of the 2D array. This ultrasound head can also be equipped with a position sensor.

Position capturing systems, as can be used in conjunction with the deployed ultrasound heads, can be based for example on magnetic or optical principles, as known to the person skilled in the art from the prior art.

With the proposed method it is not necessary to create a 3D ultrasound image in every instance. Instead a 2D ultrasound image can be displayed overlaid with a corresponding 2D cross-sectional image obtained from the 3D x-ray image data record. In principle the ultrasound images are preferably overlaid with the x-ray images in such a manner that the transparency of at least one of the images can be adjusted for the user. During overlaying the 2D or 3D ultrasound images can be overlaid with the 3D x-ray image or an image obtained therefrom or even just with the segmented image of the target region. The advance of the interventional instrument, in particular a puncture or biopsy needle, is monitored in this process in real time using the ultrasound images. The target region, for example a tumor, can be highlighted in this process by being displayed in color.

It is optionally possible, for example if a patient moves, for the image data to be newly recorded and/or for a new registration to take place. A new 3D image data record can thus be recorded using the x-ray system. This can be done with low or high resolution. Additionally or alternatively thereto new 3D ultrasound images or 2D ultrasound images can also be recorded.

In a further possible embodiment patient or organ movement, for example of the lung or diaphragm, can be captured by position sensors positioned in or on the patient. Registration of the imaging system can then be updated or said system can be newly registered on the basis of this movement information. The originally created 3D image data record or part of it can also distorted appropriately in order to adjust it to the extension and position of the target region, which may be been changed by the movement. In another variant after such movement has been captured, new image data can be recorded, which then replaces the originally created 3D image data record or part thereof.

The proposed method allows simpler and more precise registration of the imaging systems and as a result greater puncture accuracy to be achieved. All modalities are accessible in one room, without having to move the patient from room to room. This simplifies the workflow. Ultrasound imaging during the intervention minimizes the ionizing radiation load on the patient. The 3D x-ray image data record created before the intervention can also be used to plan the intervention, so there is no need for the previously standard creation of a CT image data record for pre-intervention planning. The merging of x-ray image data and ultrasound image data increases the advantages of both imaging modalities.

BRIEF DESCRIPTION OF THE DRAWINGS

The proposed method is described again below by way of example with reference to an exemplary embodiment in conjunction with a figure. The figure shows a schematic diagram of the sequence during implementation of the proposed method, with optional steps or paths being shown with a broken line.

DETAILED DESCRIPTION OF THE INVENTION

The workflow of the proposed method is described here with reference to a liver biopsy. The workflow comprises the following steps:
Step 1: Recording and reconstruction of a 3D DynaCT data record of the liver with high resolution; segmentation of the target region, for example a tumor, and possibly color display in the overall DynaCT data record.
Step 2: Recording of a 3D ultrasound image using an appropriate ultrasound head for 3D imaging or a number of 2D ultrasound images for a known spatial position of the ultrasound head; optionally segmentation of the target region in said ultrasound images.
Step 3: Registration of the recorded ultrasound images (2D or 3D) with the DynaCT data record.
Step 4: Needle advance with image monitoring until the needle has reached the target region in the liver.

The color display of the tumor in step 1, which can be an option, serves to enhance the identifiability of the tumor for the user in the respective image display. Segmentation here can be carried out manually or semi-automatically or automatically using known segmentation techniques. The biopsy can be planned after the recording and reconstruction of the 3D x-ray image data record (DynaCT data record).

One or more 3D ultrasound images or the individual 2D ultrasound images can be recorded with appropriate ultrasound systems in each instance, as already mentioned for example in the description above.

Different techniques can be used for the registration in step 3. Thus registration can take place for example on the basis of anatomical landmarks. These are selected by the physician in both the image data records to be registered, i.e. the ultrasound image and the x-ray image. This determines the transformation from one image to the other. A further possibility is that of carrying out a gray-scale-intensity-based 3D/3D image registration. Various automatic methods are available for this, as for example described in Joseph V. Hajnal et al., "Medical Image Registration", CRC, pages 39 to 70, 2001. The disclosure content of this publication is incorporated in the present patent application in respect of the description of the registration methods. One of the 3D images can also be replaced by a series of 2D images when implementing these methods.

A further possibility for registration is a surface adjustment of the two images to be registered after segmentation of the ROI (ROI: Region of Interest), for example of the tumor. Here the tumor serves as the central information for determining the transformation. Position sensor-based registration is also possible in cases where an ultrasound head with a position sensor is deployed. The associated location system is connected permanently to the x-ray system so that the position of the ultrasound head in the coordinate system of the x-ray system is known at all times.

There are various possible visualization alternatives for monitoring the image of the needle advance in step 4. According to one alternative each 2D real-time ultrasound image can be displayed overlaid with a corresponding 2D DynaCT cross-sectional image. This is particularly advantageous when using a location system with the ultrasound head or in instances where the ultrasound head is not moved or is only moved mechanically and in a monitored or reproducible manner. If a two-dimensional ultrasound image intersects the DynaCT volume, this section also produces a two-dimensional DynaCT image, referred to above as a 2D DynaCT cross-sectional image. The displays of the two images can be overlaid or next to each other on one or two image display facilities, in particular a monitor. One of the images can be displayed as semi-transparent, it being possible for the degree of transparency either to be selected automatically as a function of the gray-scale or to be defined by the user.

In a further visualization alternative the segmented tumor in 3D is inserted into the merged DynaCT and real-time ultrasound images or into the merged real-time ultrasound images. This is the information relating to the segmented tumor tissue or other segmented structures. On the one hand the ultrasound image can hereby overlay the segmented structures in three-dimensional space, so that the visualization can be freely rotated in space. On the other hand the segmented structure can overlay the plane of the 2D ultrasound image appropriately. If the segmented structure does not intersect the ultrasound image, at least its projection or distance can be visualized. Such a visualization can be understood for example from the publication by Björn Meyer et al., "Schichtbasierte Illustration medizinischer Volumendaten zur intraoperativen Navigation" (Layer-based illustration of medical volume data for intra-operative navigation), in: Proceedings: Bildverarbeitung für die Medizin (BVM) (Medical Image Processing) 2006, pages 335-339, Springer 2006, the disclosure content of which is incorporated in the present patent application. This visualization serves to provide the user with depth information, allowing said user better to estimate how deep the needle is in the tumor tissue.

In a further visualization alternative the ultrasound images are overlaid directly in the 3D DynaCT data record.

Two separate screens can also be used for simultaneous visualization of the 3D and 2D image data.

While the intervention is being carried out, in other words while the needle is advancing with image monitoring, image data can be newly recorded or new registration can take place. In some circumstances the needle advance results in distortion of the structures to be punctured in the organ. By newly recording a low-resolution DynaCT data record, it is possible to estimate the distortion field and apply this to the first high-resolution DynaCT data record, to provide more realistic imaging for the further advance of the needle. The first high-resolution DynaCT data record is hereby modified using information about the distortions.

In a further embodiment a new DynaCT data record can be recorded with high resolution. This further high-resolution DynaCT data record then replaces the previously created high-resolution DynaCT data record completely. The current DynaCT data record in each instance is newly registered and merged with the ultrasound images here. This also happens if there is no new DynaCT recording, just new registration. If an ultrasound head is used, which is used to generate 3D ultrasound images, continuous image-based registration of the current 3D ultrasound images with the DynaCT data record can take place, since this provides sufficient image information for registration. Alternatively movement of the patient or organ and/or the resulting distortion of the region of interest can also be captured by additional position sensors, which are then used as the basis for the new registration.

The invention claimed is:

1. A method for assisting a percutaneous intervention, comprising:
   recording a plurality of 2D x-ray images of an object region of a patient before the intervention with a first resolution at a plurality of different projection angles;
   reconstructing a first 3D image data of the object region from the 2D x-ray images;
   performing the percutaneous intervention with an interventional instrument having a needle that is advanced to perform a biopsy and/or puncture in the object region of the patient;
   recording an ultrasound image containing a part of the object region before and/or during the intervention with a second resolution;
   registering the ultrasound image with the 3D image data;
   overlaying the ultrasound image with the 3D image data for guiding the needle, wherein advancement of the needle causes structural distortion in the object region of the patient;
   generating a new 3D image data configured with a resolution that is lower than the first resolution to estimate a distortion field in the object region of the patient;
   applying the estimated distortion field to the first 3D image data of the object region to provide a distortion-adjusted 3D image data configured to account for the structural distortion in the object region of the patient; and
   overlaying the ultrasound image with the distortion-adjusted 3D image data for monitoring further advancement of the needle.

2. The method as claimed in claim 1,
   wherein the ultrasound image is a 2D ultrasound image and is overlaid with a corresponding 2D cross-sectional image from the 3D image data, and
   wherein the overlaid image is displayed.

3. The method as claimed in claim 1, wherein a transparency of the ultrasound image or the 3D image data is adjusted during overlaying.

4. The method as claimed in claim 1, wherein a plurality of 2D ultrasound images are recorded by an ultrasound head at a plurality of recording positions and are lined up with one another according to the recording positions to generate a 3D ultrasound image data record.

5. The method as claimed in claim 4, wherein the ultrasound head is moved by a machine or manually between the recordings.

6. The method as claimed in claim 4, wherein the ultrasound head has a position sensor for capturing the recording positions.

7. The method as claimed in claim 1, wherein a 3D ultrasound image is directly generated by an ultrasound head with a rotatable 2D ultrasound converter array via controlling a rotation of the array.

8. The method as claimed in claim 1, wherein a new 3D image data is generated and is registered with the ultrasound image if a movement of the patient or an organ of the patient influencing the target region exceeds a specific degree.

9. The method as claimed in claim 8,
wherein the new 3D image data is generated with a resolution that is lower than the first resolution, and
wherein the 3D image data recorded before the intervention is corrected based on the newly generated 3D image data.

10. The method as claimed in claim 8,
wherein the new 3D image data is generated with the first resolution, and
wherein at least some of the 3D image data recorded before the intervention is replaced with the newly generated 3D image data.

11. The method as claimed in claim 8, wherein the movement of the patient or the organ is captured by a position sensor that is positioned in or on the patient.

12. The method as claimed in claim 11, wherein the 3D image data is distorted appropriately based on the movement captured by the position sensor for adjusting the 3D image data to an extension and a position of the target region as changed by the movement.

13. The method as claimed in claim 1, wherein the second resolution is lower than the first resolution.

14. The method as claimed in claim 1, wherein the overlaid image is displayed during the intervention.

15. The method as claimed in claim 1, wherein the ultrasound image is displayed next to the 3D image data during the intervention.

16. The method as claimed in claim 1,
wherein the target region is segmented in the reconstructed 3D image data, and
wherein:
the ultrasound image is overlaid with the segmented target region and the overlaid image is displayed during the invention, or
the ultrasound image is displayed next to the segmented target region during the invention.

17. A method for assisting a percutaneous intervention, comprising:
recording a plurality of 2D x-ray images of an object target region of a patient before the intervention with a first resolution at a plurality of different projection angles;
reconstructing a 3D image data of the object region from the 2D x-ray images;
segmenting the object target region for the intervention in the reconstructed 3D image data;
performing the percutaneous intervention with an interventional instrument having a needle that is advanced to perform a biopsy and/or puncture in the object target region of a patient;
recording an ultrasound image containing a part of the object target region before and/or during the intervention with a second resolution;
registering the ultrasound image with the 3D image data;
overlaying the ultrasound image with the segmented target region for guiding the needle, wherein advancement of the needle causes structural distortion in the object target region of the patient;
generating a new 3D image data configured with a resolution that is lower than the first resolution to estimate a distortion field in the object target region of the patient;
applying the estimated distortion field to the first 3D image data of the object target region to provide a distortion-adjusted 3D image data configured to account for the structural distortion of the object target region of the patient; and
overlaying the ultrasound image with the distortion-adjusted 3D image data for monitoring further advancement of the needle.

18. The method as claimed in claim 17,
wherein the overlaid image is displayed during the invention, or
wherein the ultrasound image is displayed next to the segmented target region during the invention.

19. The method as claimed in claim 17, wherein the ultrasound image is a 3D ultrasound image and the segmented target region is inserted into the 3D ultrasound image.

20. A medical system for assisting a percutaneous intervention, comprising:
an interventional instrument configured to perform a percutaneous intervention in a patient, the interventional instrument including a needle to perform a biopsy and/or puncture in an object region of the patient;
an x-ray image recording device configured to record a plurality of 2D x-ray images of the object region of the patient before the intervention with a first resolution at a plurality of different projection angles;
an ultrasound recording device operably connected to the x-ray image recording device and configured to record an ultrasound image containing a part of the object region before and/or during the intervention with a second resolution;
an imaging processor configured to:
reconstruct a first 3D image data of the object region from the 2D x-ray images,
register the ultrasound image with the 3D image data,
overlay the ultrasound image with the 3D image data for guiding the needle, wherein advancement of the needle causes structural distortion in the object region of the patient, the image processor is further configured to:
generate a new 3D image data configured with a resolution that is lower than the first resolution to estimate a distortion field in the object region of the patient;
apply the estimated distortion field to the first 3D image data of the object region to provide a distortion-adjusted 3D image data configured to account for the structural distortion of the object region of the patient; and
overlay the ultrasound image with the distortion-adjusted 3D image data for monitoring further advancement of the needle.

* * * * *